(12) United States Patent
Kucharczyk et al.

(10) Patent No.: US 12,402,989 B2
(45) Date of Patent: Sep. 2, 2025

(54) METHOD FOR INCORPORATING PHOTOGRAPHIC FACIAL IMAGES AND OR FILMS OF A PERSON INTO THE PLANNING OF ODONTOLOGICAL AND OR COSMETIC DENTAL TREATMENTS AND OR THE PREPARATION OF RESTORATIONS FOR SAID PERSON

(71) Applicant: DENTSPLY SIRONA Inc., York, PA (US)

(72) Inventors: Ronny Kucharczyk, Worms (DE); Steffen Hauth, Mainz-Kostheim (DE); André Koza, Worms (DE)

(73) Assignee: Dentsly Sirona, Inc., York, PA (US)

( * ) Notice: Subject to any disclaimer, the term of this patent is extended or adjusted under 35 U.S.C. 154(b) by 739 days.

(21) Appl. No.: 17/279,614

(22) PCT Filed: Sep. 27, 2019

(86) PCT No.: PCT/US2019/053471
§ 371 (c)(1),
(2) Date: Mar. 25, 2021

(87) PCT Pub. No.: WO2020/072308
PCT Pub. Date: Apr. 9, 2020

(65) Prior Publication Data
US 2021/0338388 A1    Nov. 4, 2021

(30) Foreign Application Priority Data
Oct. 2, 2018   (EP) .................................. 18198342

(51) Int. Cl.
*A61C 13/00*   (2006.01)
*A61B 1/24*    (2006.01)
(Continued)

(52) U.S. Cl.
CPC ............ *A61C 13/0004* (2013.01); *A61B 1/24* (2013.01); *A61C 9/0053* (2013.01); *G06F 30/12* (2020.01);
(Continued)

(58) Field of Classification Search
CPC ......... H04N 23/64; G06F 30/12; G06T 17/00; G16H 30/20; A61C 13/0004
See application file for complete search history.

(56) References Cited

U.S. PATENT DOCUMENTS

| 2010/0076581 A1 | 3/2010 | Molante |
| 2010/0145898 A1 | 6/2010 | Malfliet et al. |

(Continued)

FOREIGN PATENT DOCUMENTS

| DE | 102015222782 | 5/2017 |
| EP | 3632369 | 4/2020 |

(Continued)

OTHER PUBLICATIONS

Korean Office Action dated Jun. 20, 2024.
(Continued)

*Primary Examiner* — John E Johansen
*Assistant Examiner* — Michael Paul Mirabito
(74) *Attorney, Agent, or Firm* — SCHWEGMAN LUNDBERG & WOESSNER, P.A.

(57) ABSTRACT

In a method for incorporating photographic facial images and/or films of a person into the preparation of odontological and/or cosmetic dental treatments and/or restorations for said person, the photographic facial images and/or films are produced using the camera function of a smart device. The user is guided through the production of the facial images and/or films with the aid of an application for the smart device, and the produced images and/or films are incorpo-
(Continued)

rated into software for a computer-assisted design of the treatments and/or restorations.

6 Claims, 3 Drawing Sheets

(51) Int. Cl.
| | |
|---|---|
| *A61C 9/00* | (2006.01) |
| *G06F 30/12* | (2020.01) |
| *G06T 17/00* | (2006.01) |
| *G16H 30/20* | (2018.01) |
| *G16H 40/20* | (2018.01) |
| *G16H 40/67* | (2018.01) |
| *H04N 23/60* | (2023.01) |

(52) U.S. Cl.
CPC ............ *G06T 17/00* (2013.01); *G16H 30/20* (2018.01); *G16H 40/20* (2018.01); *G16H 40/67* (2018.01); *H04N 23/64* (2023.01); *G06T 2200/08* (2013.01); *G06T 2210/41* (2013.01)

(56) References Cited

U.S. PATENT DOCUMENTS

| | | | |
|---|---|---|---|
| 2011/0008751 A1 | 1/2011 | Pettersson | |
| 2011/0151400 A1 | 6/2011 | Boiangiu | |
| 2013/0166312 A1 | 6/2013 | Lauciello | |
| 2014/0379356 A1 | 12/2014 | Sachdeva et al. | |
| 2015/0198943 A1* | 7/2015 | Kotlus ................... | B22F 10/80 700/98 |
| 2016/0284123 A1* | 9/2016 | Hare ........................ | G06T 7/55 |
| 2016/0317264 A1* | 11/2016 | Derraugh ............. | A61C 9/0053 |
| 2017/0035536 A1 | 2/2017 | Alvarez Garcia | |
| 2017/0049311 A1 | 2/2017 | Borovinskih et al. | |
| 2017/0319293 A1 | 11/2017 | Fisker | |
| 2018/0125610 A1 | 5/2018 | Carrier, Jr. et al. | |
| 2018/0181737 A1 | 6/2018 | Tussy | |
| 2018/0228359 A1 | 8/2018 | Meyer | |
| 2019/0231523 A1 | 8/2019 | Fabien | |

FOREIGN PATENT DOCUMENTS

| | | | | |
|---|---|---|---|---|
| JP | 1985216687 A | 9/1985 | | |
| JP | 1999001814 A | 6/1999 | | |
| JP | 2000003376 A | 1/2000 | | |
| JP | 2001522108 A | 11/2001 | | |
| JP | 2002132916 A | 5/2002 | | |
| JP | 2008210208 A | 9/2008 | | |
| JP | 2010104737 A | 5/2010 | | |
| JP | 2010524529 A | 7/2010 | | |
| JP | 2011521767 A | 7/2011 | | |
| JP | 2012500706 A | 1/2012 | | |
| JP | 2014091047 A | 5/2014 | | |
| JP | 2017221329 A | 12/2017 | | |
| JP | 2018115399 A | 7/2018 | | |
| KR | 20090132838 | 12/2009 | | |
| KR | 20110049884 | 5/2011 | | |
| WO | WO-2010008435 A1 * | 1/2010 | ......... | A61C 13/0004 |
| WO | WO-2018095293 A1 * | 5/2018 | ......... | G06K 9/00255 |
| WO | 2020072308 | 4/2020 | | |

OTHER PUBLICATIONS

International Search Report; PCT/US2019/053471; Nov. 25, 2019 (completed); Dec. 13, 2019 (mailed).
Written Opinion of the International Searching Authority; PCT/US2019/053471; Nov. 25, 2019 (completed); Dec. 13, 2019 (mailed).
International Preliminary Report on Patentability; PCT/US2019/053471; Nov. 25, 2019 (completed); Dec. 13, 2019 (mailed).
"European Application Serial No. 181983420, Extended European Search Report mailed Apr. 5, 2019", 6 pgs.
"European Application Serial No. 181983420, Response filed Oct. 8, 2020 to Extended European Search Report mailed Apr. 5, 2019", 24 pgs.
"European Application Serial No. 181983420, Communication Pursuant to Article 94(3) EPC mailed Jan. 19, 2021", 5 pgs.
"European Application Serial No. 181983420, Response filed May 20, 2021 to Communication Pursuant to Article 94(3) EPC mailed Jan. 19, 2021", 33 pgs.
"European Application Serial No. 181983420, Summons to Attend Oral Proceedings mailed Jul. 28, 2023", 11 pgs.
"Video, Dental Shooting: Tutorial 3 3 Tips and Tricks (Mobile Dental Photography)", Dental Shooting on Youtube, [Online] Retrieved from the internet:https: www.youtube.com watch?v=QaJ0O-98MFE, (Uploaded Sep. 20, 2017), 2 pgs.

* cited by examiner

METHOD FOR INCORPORATING PHOTOGRAPHIC FACIAL IMAGES AND OR FILMS OF A PERSON INTO THE PLANNING OF ODONTOLOGICAL AND OR COSMETIC DENTAL TREATMENTS AND OR THE PREPARATION OF RESTORATIONS FOR SAID PERSON

CROSS-REFERENCE TO RELATED APPLICATIONS

This is a National Phase application of International Application No. PCT/US2019/053471, filed Sep. 27, 2019, which claims the benefit of and priority to EP Application Ser. No. 18198342.0, filed on Oct. 2, 2018, which are herein incorporated by reference for all purposes.

TECHNICAL FIELD

The invention relates to a method for incorporating photographic facial images and/or films of a person into the planning of odontological and/or cosmetic dental treatments and/or the preparation of restorations for said person, as well as to an application for a smart device and a computer program for a computer-assisted design of odontological and/or cosmetic dental treatments and/or restorations.

BACKGROUND OF THE INVENTION

For the production of odontological and/or cosmetic dental restorations, for example crowns, bridges or veneers, photographic representations of the face and/or the mouth region of the person to be treated are very helpful to the dental technician and the dentist. Photographs are very important, in particular for the restoration or creation of an aesthetically pleasing and also functional smile. The color, shape and size of the teeth, the coordination with the shape and color of the face, the smile line, the position of the eyes and the position of the midline, in particular, play an important part in being able to produce an aesthetically pleasing restoration. The color of the gingiva and the positioning of the teeth also contribute to a smile being subjectively perceived as pleasing. For this reason, even in the analog era, it has long been a practice to produce two-dimensional photographs of the person to be treated and provide them to the dental technician.

Newer digital methods use a computer-assisted design of treatment plans and restorations (CAD/CAM technology) to provide optimum restorations for the patient, for example on the basis of tooth libraries or biogenerically calculated tooth models. Photographs of the person to be treated can be incorporated into such digital methods and, for example, be transferred and converted into three-dimensional models. The conversion of a two-dimensional photograph into a three-dimensional representation can be accomplished, for example, by stretching the two-dimensional representation over a template. The traditional recommendation is to produce the photographs using a single-lens reflex (SLR) camera. The data is then transmitted via a data export, for example from the digital single-lens reflex camera, and an import to the computer on which the CAD software is installed.

It is also possible, for example, to incorporate three-dimensional facial scans into such computer programs. In terms of the required scanner, however, this is very expensive. X-ray-based, three-dimensional systems are another option; however, due to the radiation exposure, these could be rather more detrimental to the person in question.

DE 10 2015 222 782 A1 describes a method for visualizing a tooth situation, wherein an image of the face of a patient is recorded and stored as a facial data set. The facial data set can be two-dimensional or three-dimensional. Such data sets allow the current and the planned tooth situation to be visualized for the patient as well. Furthermore, the course of a treatment, for example an orthodontic treatment, can be tracked as well. Such methods are also suitable for the so-called Smile Design (SD), by means of which the targeted result of an odontological and/or cosmetic dental treatment is visualized.

US 2017/0049311 A1 describes methods and systems for following the progress of a dental treatment, wherein one or more two-dimensional photographs of the patient, more specifically his teeth, are taken and incorporated into the observation system. The photographs can be taken using a mobile phone (smartphone), wherein it can be provided that the user receives instructions to record the photograph in a specific standard view.

The underlying object of the present invention is to improve the incorporation of digital images into software for computer-assisted design and/or for planning odontological and/or cosmetic dental treatments and/or restorations and to make it more user-friendly.

SUMMARY OF THE INVENTION

This object is achieved by a method, as well as by an application for a smart device and a computer program, as is the subject matter of the claims. The method is provided for incorporating photographic facial images and/or films of a person into the planning and/or preparation of odontological and/or cosmetic dental treatments and/or restorations for said person, wherein the photographic facial images and/or films are produced using the camera function of a smart device. The term "smart device" includes mobile, electronic devices with computer functionalities. It is essential to the invention that the smart device comprises a camera function, wherein preferably one (or more) high-resolution camera functions are available. Examples of suitable smart devices are in particular smartphones, but also tablets, smart watches or the like if a camera function is available. The odontological and/or cosmetic dental treatments can in particular be orthodontic treatments. Odontological and/or cosmetic dental restorations are artificial tooth replacement products such as inlays, crowns, bridges or veneers. Photographic facial images and/or films are two-dimensional or, if applicable, also three-dimensional digital recordings, i.e. photographs or films (videos), of the entire face or the head or even only the mouth region, for example. The key aspect of the invention is that the user, i.e. the person who records the photographs or films, is guided through the production of the facial images and/or films with the aid of an application for the smart device, and the produced images or films are incorporated into software for a computer-assisted design of the restorations and/or the treatment planning. The particular advantage of this method is that the treating dentists and/or the staff of a dental or an orthodontic practice usually already have suitable smart devices, which are equipped with a high-quality and often high-resolution camera. Since the image quality of modern smart device cameras is generally very high, the camera function of smart devices, in particular smartphones, is already used frequently for documentation purposes, so that the single-lens reflex cameras typically used in the past are no longer necessary. In addition, smart devices generally provide very workable archiving functions, which are used in dental or orthodontic practices. One problem with the past use of smart devices for the production of photographs, however, is that the photographs may be unsuitable or inadequate for digital further processing as a result of unfavorable recording angles, unsuitable light conditions or the like. The invention solves this problem by guiding the user through the production of the facial images and/or films with the aid of an application for the smart device. The application provides the user with information on how suitable photographs or films are to be produced. This ensures that the condition of the photographs or films is such that the software for a computer-assisted design of the restorations or treatment plans can easily process said images or films.

The software supports the computer-assisted design of the restorations and/or of the treatment plans (CAD). It can also be a program with which the production of the restorations is carried out in a computer-assisted manufacturing (CAM) as well. Combined programs, so-called CAD/CAM systems are particularly preferred. In the following, the software for the computer-assisted design of the restorations is also generally referred to as CAD software; this can, however, also refer to a CAD/CAM system.

In this context, an application is a so-called app, which refers to an application software for smart devices (mobile devices) or for mobile operating systems.

The communication between the application and the CAD software and/or the transmission of data between the application and the CAD software, i.e. the participating devices (smart device and computer, for example) is preferably wireless, whereby the data can flow in both directions. The image or film data can thus be transmitted from the smart device to the computer with the CAD software without any additional effort on the part of the user in a very user-friendly and preferably automatic manner. Wireless communication furthermore offers the option of providing feedback on whether or not the recorded photographs or films are suitable to the user by means of the CAD program virtually in real time.

A template for the positioning of the face and/or of the mouth region is preferably provided in the display of the smart device for the guidance through the production of the facial images, so that the face is exactly centered in the photograph or the film, for example. It can furthermore be specified that the person or the face of the person be recorded in different positions, for example from the front, in semi-profile or in profile. It can furthermore be specified that the person be recorded with and without a cheek retractor and/or that the person be recorded smiling and not smiling, if applicable respectively with and without a cheek retractor. It can furthermore be specified that the person be recorded from a specific perspective. It can also be provided that the person be recorded from different perspectives and, if applicable, in different positions, wherein photos or films are to be recorded, for example, with the mouth closed, with the mouth open, smiling, not smiling, with a cheek retractor and without a cheek retractor. The application can furthermore specify that particular light conditions are to be set for the recording. The method can be configured in such a way that instructions to use or start the application on the smart device are provided via the software that carries out the computer-assisted design, so that the user is prompted to record photographs or films of the face and/or the mouth region of the person to be treated with the smart device in a suitable manner and start the application on the smart device for this purpose. An automatic start can be provided on the smart device as well.

One or more check functions can furthermore be provided in the CAD software or also in the application on the smart device, which check, and preferably communicate, to the user, whether the facial images or films produced with the aid of the application with the smart device satisfy the requirements of the CAD software. Thus, if necessary, the user can be prompted to repeat the production of the recordings. Instructions regarding changes or improvements that should be made, for example changing the image detail, changing the light conditions, changing the position or perspective during the recording or the like, can be provided as well. The check function can also include a light measurement or a contrast measurement, for example, so that optimally lit images or films can be obtained.

In a particularly preferred embodiment of the method according to the invention, the photographic facial images and/or films are incorporated into a digital visualization of the targeted result of the odontological and/or cosmetic dental treatments and/or restorations in the CAD software. The photographic facial images and/or films are preferably incorporated into the production of a three-dimensional image or model of the face and/or the mouth region of the person. The facial images and/or films can particularly advantageously be incorporated into a Smile Design in the CAD software. For this purpose, it can be provided that the user is prompted to start the relevant application on the smart device when he calls up the per se known function of the Digital Smile Design in the corresponding CAD program, wherein further instructions to guide the user through the production of optimum recordings for the software can then be issued in both the CAD software and the application.

In a preferred embodiment of the method, it can be provided that the resulting information and data relating to the restorations to be made, which have been produced using the CAD software, are forwarded to a dental facility for making the restorations. The same applies to orthodontic appliances which can be designed in the context of treatment planning. This can be carried out in an automated manner, for example by incorporation via an online portal, which makes the flow of information to a technical laboratory possible in a very user-friendly manner.

The invention further relates to an application for a smart device, wherein the application is designed to carry out the described method.

Finally, the invention includes a computer program for a computer-assisted design of odontological and/or cosmetic dental treatments and/or restorations, wherein the described method and/or the described application for the smart device are incorporated into the computer program. Said computer program allows the user to incorporate digital recordings (images and/or films) of the face and/or the mouth region into the design and the production of the restorations and/or treatment plans in an optimum and very user-friendly and convenient manner. In addition, by the use of the computer program and the application for the smart device, errors in the production of the photos or films can be avoided or corrected immediately.

BRIEF DESCRIPTION OF THE DRAWINGS

Design examples of the invention are shown in the drawings and explained in more detail in the following description. The individual features can hereby be realized individually or in combination with one another.

DETAILED DESCRIPTION OF THE INVENTION

Figure 1:
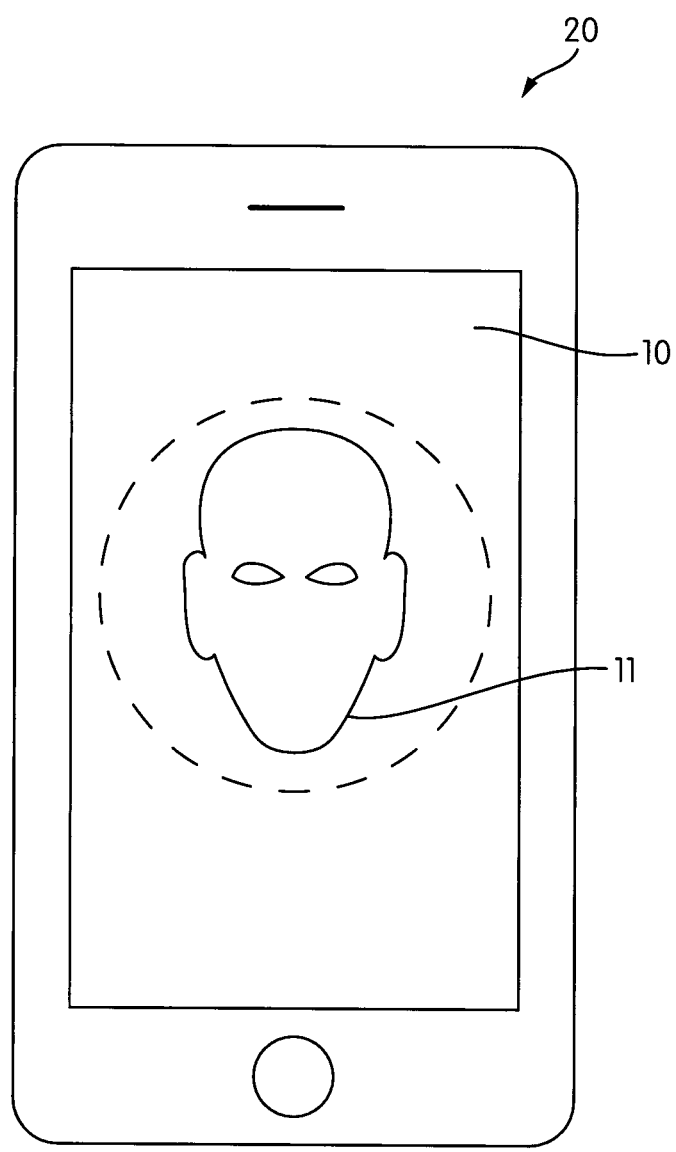
FIG. 1 schematic representation of the user interface of a smart device during the course of the application according to the invention with the specification of a template for the image of the face.
Figure 2:
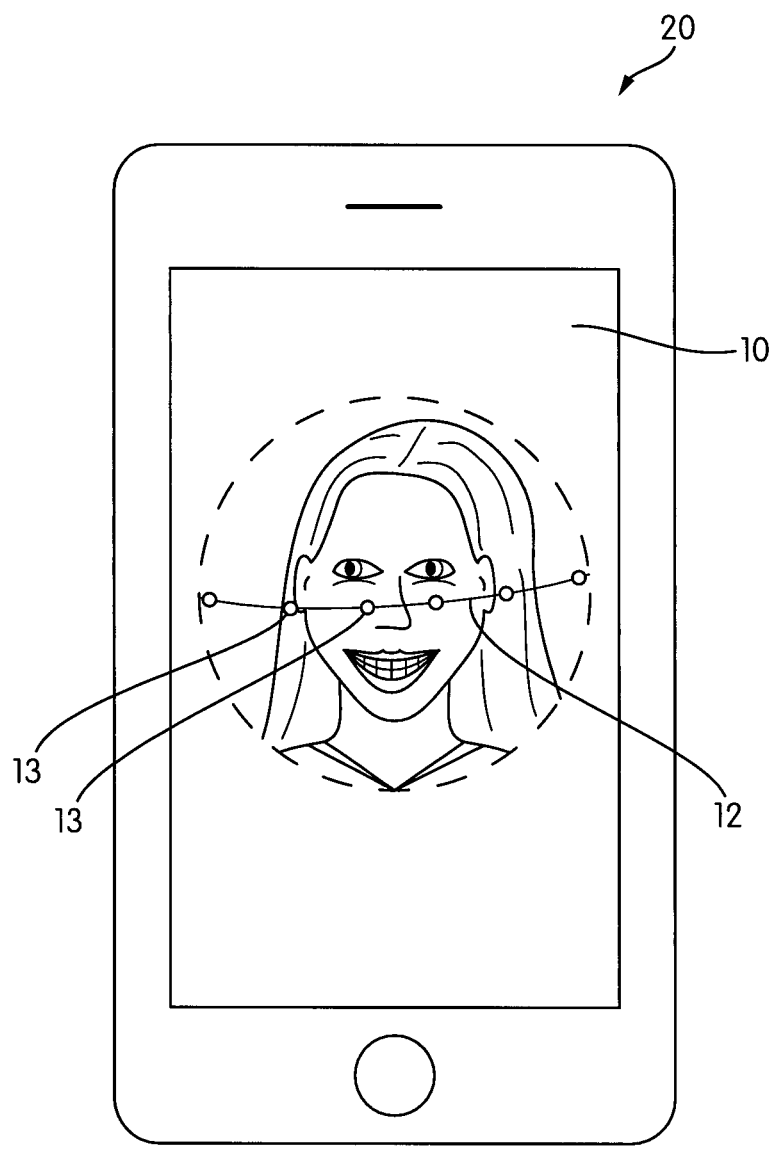
FIG. 2 schematic representation of the user interface of a smart device during the course of the application according to the invention with the specification of recording positions for the image of the face and FIG. 3 schematic flow chart of the method for incorporating digital images of the face according to the invention.

FIG. 1 schematically shows the user interface 10 of a smart device 20, the camera function of which is used to produce photographic images of the face (digital facial images and/or facial films). The smart device 20 in this example is a mobile phone. The figure illustrates a view of the application for the smart device 20 within the camera function of said smart device, by means of which the user is guided through the production of optimum images of the face. The produced images or films can thus be incorporated into software for a computer-assisted design of odontological and/or cosmetic dental treatment plans and/or restorations in a very user-friendly manner. At the same time, appropriate specifications and check functions of the application can ensure that optimum photographic recordings (images or films or videos), which are suitable for digital further processing within the CAD software, are produced. By means of the scene within the application shown in FIG. 1, with the display of a template 11 in the form of a mask, the user is prompted to position the face to be recorded in a correspondingly centered manner when recording. In the further course of the application, by changing the template 11, the user can be prompted to change the position of the head to be photographed or recorded; for example, to generate recordings in full profile and in semi-profile. If, within the framework of the application, not only images but alternatively or additionally films or videos are recorded, the user can be prompted, for example, by the display of arrows, to have the person to be recorded turn his head or to move the smart device 20 accordingly. FIG. 2 illustrates a scene within the application, wherein position points 13 are displayed along a central line 12 on the user interface 10 of the smart device 20, by means of which the user is prompted to take images at the various positions by moving the smart device 20. In order to generate image data for the production of a complex three-dimensional model, the user can further be prompted to also take images from positions above and below the central line 12 by means of arrows or the like. Additional prompts can further be directed to the user within the framework of the application, for example asking the person to be recorded to smile (with open or closed mouth) and/or to use a cheek retractor. These prompts can, for example, be in writing, visual or even audible.

Figure 3:
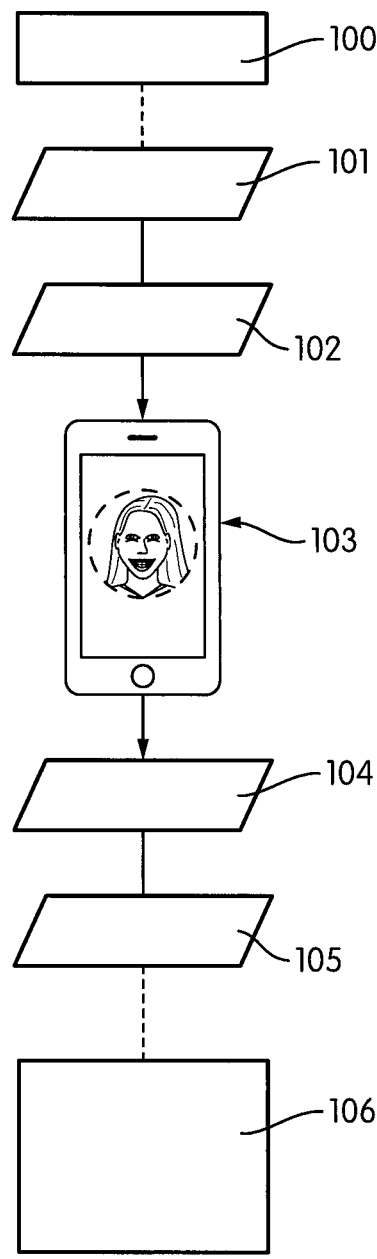

FIG. 3 schematically illustrates a possible flow chart for carrying out the method for incorporating the photographic facial images and/or films into a computer-assisted design of restorations and/or treatment plans (CAD software). The first step is the start 100 of the CAD software. Within the running of the program, the user can be asked whether a Digital Smile Design is to be carried out (Step 101). If this feature is requested, the user is asked to start the relevant application on a smart device (Step 102). The required instructions can subsequently be provided in both the CAD software and in the application. After the start of the application, the user is guided through the production of digital images of the face (images or films or videos) with the aid of appropriate prompts on the display of the smart device within the framework of the application according to the invention (Step 103). By means of a type of template in the camera function of the smart device, the user can be advised how to position the camera or the smart device to take an image that is ideal for the CAD software. This process is preferably repeated for a number of perspectives. This is preferably carried out with feedback or in mutual communication with the CAD software. The application of the smart device and the CAD software can preferably communicate with one another wirelessly, for example by means of integrated radio modules. It is, in particular, possible to check whether or not the recordings are suitable for further digital processing virtually in real time. If, within the context of a check function, it is for example determined that a recording is unsuitable, this can be displayed to the user immediately, so that the user has the opportunity to repeat and, if necessary, improve the recording. After and/or during the production of the facial images, the relevant data is transmitted to the CAD software or to a corresponding computer, on which the software is installed and runs (Step 104). The digital images of the face are incorporated in the CAD software, wherein the data can in particular be converted into a three-dimensional representation (model) (Step 105). The user can then continue the familiar digital design process for restorations and/or treatment plans in the CAD software, wherein the additional information of digital images of the face of the patient is now contained and incorporated here. A visualization of the data of the two-dimensional facial image or film, for example, that has been included in a three-dimensional representation, can subsequently be displayed. The user can thus, for example, design the restorations in such a way that they combine to an aesthetically pleasing smile and, at the same time, within the framework of a Digital Smile Design, for example provide the patient with a realistic preview of his future restoration (Step 106).

In order to provide this information to a dental technician so he can carry out the actual production of the restorations and/or treatment devices on this basis, the results of the CAD software, i.e. the design of the restorations and/or the orthodontic treatment plans, for example, can be forwarded, for example via an online portal.

The invention claimed is:

1. Method for incorporating photographic facial images and/or films of a person into the planning of odontological and/or cosmetic dental treatments and/or the preparation of restorations for said person, comprising:
    producing the photographic facial images and/or films using a camera function of a smart device, a user being guided through the production of the photographic facial images and/or films with the aid of an application for the smart device by:
        providing guidance on a positioning of the smart device for taking a first photographic facial image and/or film in a first perspective using a template, wherein guidance through the production of the photographic facial images and/or films specifies the recording of the person in different positions by:
            providing a central line on an interface of the smart device, the central line comprising a plurality of visualized position points:

wherein the smart device is successively moved to corresponding to the visualized position points and the photographic facial images and/or films are generated, wherein additional photographic facial images and/or films are generated for positions above and below the central line;

generating the first photographic facial image and/or film;

based on feedback, changing the template to provide guidance on the positioning of the smart device for taking a second or other photographic facial image and/or film in a different perspective;

generating the second or other photographic facial image and/or film:

performing, in real time, a suitability check about a suitability of the photographic facial images and/or films for digital processing, the suitability check including at least a check for an image detail, and a check for a lighting condition;

responsive to determining that at least one of the photographic facial images and/or films fails the suitability check, providing additional guidance for repeating and improving the at least one of the photographic facial images and/or films;

generating a three-dimensional model by converting the photographic facial Images and/or films into the three-dimensional model;

responsive to generating the three-dimensional model, digitally designing a restoration and/or treatment plan using the three-dimensional model, a visualization of the photographic facial images and/or films being used in the digitally designing;

wherein the method further comprises providing guidance for recording a smile and for using a cheek retractor; and generating corresponding photographic facial images and/or films which are additionally used in generating the three-dimensional model.

2. Method according to claim 1, further comprising incorporating the photographic facial images and/or films into software for a computer-assisted design of the treatments and/or restorations, wherein the application for the smart device and the software communicate with and/or transfer data to one another wirelessly.

3. Method according to claim 2, wherein in the software, the photographic facial images and/or films are incorporated into a digital design of a smile.

4. Method according to claim 2, wherein information from the computer-assisted design of the treatments and/or restorations is forwarded to a dental facility.

5. A non-transitory computer-readable medium storing instructions which when executed cause a computer system to:

produce photographic facial images and/or films using a camera function of a smart device, a user being guided through the production of the photographic facial images and/or films with the aid of an application for the smart device by:

providing guidance on a positioning of the smart device for taking a first photographic facial image and/or film in a first perspective using a template, wherein the guidance comprises:

providing a central line on an interface of the smart device, the central line comprising a plurality of visualized position points;

wherein the smart device is successively moved to corresponding to the visualized position points and the photographic facial images and/or films are generated, wherein additional photographic facial images and/or films are generated for positions above and below the central line;

generating the first photographic facial image and/or film;

based on feedback, changing the template to provide guidance on the positioning of the smart device for taking a second or other photographic facial image and/or film in a different perspective;

generating the second or other photographic facial image and/or film;

performing, in real time, a suitability check about a suitability of the photographic facial images and/or films for digital processing, the suitability check including at least a check for an image detail, and a check for a lighting condition;

responsive to determining that at least one of the photographic facial images and/or films fails the suitability check, providing additional guidance for repeating and improving the at least one of the photographic facial images and/or films;

generating a three-dimensional model by converting the photographic facial Images and/or films into the three-dimensional model;

responsive to generating the three-dimensional model, digitally designing a restoration and/or treatment plan using the three-dimensional model, a visualization of the photographic facial images and/or films being used in the digitally designing;

further comprising providing guidance for recording a smile and for using a cheek retractor; and generating corresponding photographic facial images and/or films which are additionally used in generating the three-dimensional model.

6. A computer system comprising a smart device and a processor configured to:

produce photographic facial images and/or films using a camera function of a smart device, a user being guided through the production of the photographic facial images and/or films with the aid of an application for the smart device by:

providing guidance on a positioning of the smart device for taking a first photographic facial image and/or film in a first perspective using a template, wherein the guidance comprises:

providing a central line on an interface of the smart device, the central line comprising a plurality of visualized position points:

wherein the smart device is successively moved to corresponding to the visualized position points and the photographic facial images and/or films are generated, wherein additional photographic facial images and/or films are generated for positions above and below the central line;

generating the first photographic facial image and/or film;

based on feedback, changing the template to provide guidance on the positioning of the smart device for taking a second or other photographic facial image and/or film in a different perspective;

generating the second or other photographic facial image and/or film;

performing, in real time, a suitability check about a suitability of the photographic facial images and/or films for digital processing, the suitability check including at least a check for an image detail, and a check for a lighting condition;

responsive to determining that at least one of the photographic facial images and/or films fails the suitability check, providing additional guidance for repeating and improving the at least one of the photographic facial images and/or films;

generating a three-dimensional model by converting the photographic facial images and/or films into the three-dimensional model;

responsive to generating the three-dimensional model, digitally designing a restoration and/or treatment plan using the three-dimensional model, a visualization of the photographic facial images and/or films being used in the digitally designing;

further comprising providing guidance for recording a smile and for using a cheek retractor; and generating corresponding photographic facial images and/or films which are additionally used in generating the three-dimensional model.

\* \* \* \* \*